(12) United States Patent
Peterson

(10) Patent No.: US 6,359,195 B1
(45) Date of Patent: Mar. 19, 2002

(54) ALFALFA LINE CALLED WL-W316 AND METHOD FOR PRODUCING SAME

(75) Inventor: Michael A. Peterson, Janesville, WI (US)

(73) Assignee: W-L Research, Inc., Madison, WI (US)

( * ) Notice: Subject to any disclaimer, the term of this patent is extended or adjusted under 35 U.S.C. 154(b) by 0 days.

(21) Appl. No.: 09/346,188

(22) Filed: Jul. 1, 1999

(51) Int. Cl.⁷ .................................................. A01H 5/10
(52) U.S. Cl. ...................................................... 800/265
(58) Field of Search ................................ 800/265, 295, 800/298, 260

(56) References Cited

U.S. PATENT DOCUMENTS

| | | | |
|---|---|---|---|
| 5,075,217 A | 12/1991 | Weber | 435/6 |
| 5,324,631 A | 6/1994 | Helentjaris et al. | 436/6 |
| 5,324,646 A | 6/1994 | Buising et al. | 435/172.3 |
| 5,364,759 A | 11/1994 | Caskey et al. | 435/6 |
| 5,385,835 A | 1/1995 | Helentjaris et al. | 435/172.3 |
| 5,451,705 A | 9/1995 | Larkins et al. | 800/200 |
| 5,492,547 A | 2/1996 | Johnson | 47/58 |
| 5,574,210 A | 11/1996 | Saghai-Maroof et al. | 800/200 |
| 5,582,979 A | 12/1996 | Weber | 435/6 |
| 5,675,066 A | 10/1997 | Stucker | 800/200 |

OTHER PUBLICATIONS

"Standard Tests to Characterize Alfalfa Cultivars", North American Alfalfa Improvement Conference, 3rd Edition, D1 to A8, (1996).

Armstrong, C.L., et al., "Establishment and Maintenance of Friable, Embryogenic Maize Callus and the Involvement of L–Proline", *Planta*, 164, 207–214, (1985).

Bedard, F., "A Whitefly Wipeout", *Haymaker*, 11, (Spring 1992).

Behling, A., "New Alfalfa Germplasm Resists Whiteflies", *Hay & Forage Grower*, 6, (Mar. 1997).

Bingham, E., et al., "Breeding Alfalfa which Regenerates from Callus Tissue in Culture", *Crop Science*, 15, 719–721, (1975).

Chu, C., et al., "Establishment of an Efficient Medium for Another Culture of Rice Through Comparative Experiments on the Nitrogen Sources", *Scientia Sinica*, 18, 659–668, (Sep.–Oct. 1975).

Coe, E., et al., "The Genetics of Corn", In: *Corn and Corn Improvement*, Third Edition, Sprague, G. F., et al., (eds.), American Society of Agronomy, Inc., Madison, WI, 81–258, (1988).

Duvick, D., "Genetic Contributions to Yield Gains of U.S. Hybrid Maize, 1930–1980", *Genetic Contributions to Yield Gains of Five Major Crop Plants*, W.R. Fehr, ed., CSSA Special Publication No. 7, 15–47, (1981).

Elgin, Jr., J.H., "Inheritance of Stem–Nematode Resistance in Alfalfa", *Crop Science*, 19, 352–354, (1979).

Elgin, Jr., J.H., et al., "Inheritance of Resistance to Race 1 and Race 2 Anthracnose in Arc and Saranac AR alfalfa", *Crop Science*, 25, 861–865, (1985).

Elgin, Jr., J.H., et al., "Use of Strain Crosses in the Development of multiple pest resistant alfalfa with improved field performance", *Crop Science*, 23, 57–64, (1983).

Fehr, W.R., "Principles of Cultivar Development", McGraw–Hill, Inc., pp. 60, 152–153, 422, (1987).

Finkle, B.J., et al., "Growth and Regeneration of Alfalfa Callus Lines After Freezing in Liquid Nitrogen", *Plant Science*, 42, 133–140, (1985).

Fuentes, S.I., et al., "Embryogenic response of Mexican alfalfa (*Medicago sativa*) varieties", *Plant Cell, Tissue and Organ Culture*, 34, 299–302, (1993).

Goodman, M., et al., "Genetic Identification of Lines and Crosses Using Isoenzyme Electrophoresis", Report of 35th Annual Corn and Sorghum Research Conference, Chicago, IL, 10–31, (Dec. 9–11, 1980).

Gordon–Kamm, W.J., et al., "Transformation of Maize Cells and Regeneration of Fertile Transgenic Plants", *The Plant Cell*, 2, 603–618, (Jul. 1990).

Hanson, A.A., et al., "Regeneration of "WL 605" Alfalfa", *Crop Science*, 27, 1084, (1987).

Hauptmann, R.M. et al., "Evaluation of Selectable Markers for Obtaining Stable Transformants on the Gramineae", *Plant Physiol.*, 86, 602–606, (1988).

Hernandez–Fernandez, M., et al., "Inheritance of Somatic Embryogenesis in Alfalfa (*Medicago sativa* L.)", *Genome*, 32, 318–321, (1989).

Klein, T.M., et al., "Genetic Transformation of Maize Cells by Particle Bombardment", *Plant Physiology*, 91, 440–444, (1989).

Lee, M., "Inbred Lines of Maize and Their Molecular Markers", *The Maize Handbook*, Freeling, et al., eds., Springer–Verlag, New York., 423–432, (1994).

(List continued on next page.)

*Primary Examiner*—Bruce R. Campell
(74) *Attorney, Agent, or Firm*—Schwegman, Lundberg, Woessner & Kluth, P.A.

(57) ABSTRACT

An improved synthetic alfalfa variety called WL-W316, and method for producing same. One embodiment provides a semidormant, Dormancy-Group-3-type synthetic alfalfa variety, wherein one embodiment is named WL-W316, that provides greater feed value and improved yields under a variety of environmental conditions and, in particular, better resistance to the wet soil pathogen Race 2 Aphanomyces root rot. The primary uses of this WL-W316 variety are hay, haylage, greenchop and dehydrated feed for livestock. The present invention also provides a method for breeding and selecting alfalfa in order to obtain resistance or high resistance to certain alfalfa pests, along with high yield and high quality. In particular, this method obtains a semidormant alfalfa variety that is high in forage quality and resistant to Race 2 Aphanomyces root rot.

35 Claims, 15 Drawing Sheets

Munkvold, G., "Alfalfa seedling diseases", http://www.ipm.iastate.edu/ipm/icm/1997/4-21-1997/alfalfa.html, pp. 1–2, (Apr. 1997).

Murashige, T., et al., "A Revised Medium for Rapid Growth and Bio Assays with Tobacco Tissue Cultures", *Physiol. Plant.,* 15, 473–497, (1962).

Ray, I., et al., "Cell Biology & Molecular Genetics : Breeding Diploid Alfalfa for Regeneration from Tissue Culture", *Crop Science,* 29, 1545–1548, (1989).

Rhodes, C.A., et al., "Genetically Transformed Maize Plants from Protoplasts", *Science,* 240, 204–207, (Apr. 1988).

Roberts, R., "Restriction and Modification Enzymes and Their Recognition Sequences", *Nucleic Acids Research,* 10, r117–r144, (1982).

Seitz Kris, M., et al., "Interactions of Highly Regenerative Genotypes of Alfalfa (*Medicago Sativa*) and Tissue Culture Protocols", *In Vitro Cellular & Developmental Biology,* 24, 1047–1052, (1988).

Smith, S.E., et al., "Morphological and Agronomic Affinities among Middle Eastern Alfalfas—Accessions from Oman and Yemen", *Crop Science,* 28, 1188–1194, (1995).

Staub, J.E., et al., "Genetic Markers, Map Construction, and Their Application in Plant Breeding", *Hort. Science,* 31(5), 729–738, (1996).

Teuber, L., et al., "Breeding Alfalfa for Resistance to the Silverleaf Whitefly", Proceedings: 27th California Alfalfa Symposium, Visalia, CA, 179–188, (Dec. 10–11, 1997).

Troyer, A., "A Retrospective View of Corn Genetic Resources", *The Journal of Heredity,* 81, 17–24, (1990).

Withers, L., et al., "Proline: A Novel Cryoprotectant for the Freeze Preservation of Cultured Cells of *Zea mays* L.", *Plant Physiology,* 64, 675–678, (1979).

Woodward, Jr., W.T., et al., "Registration of '5929' Alfalfa", *Crop Science,* 28, 186, (1988).

ANTHRACNOSE (RACE 1)
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1998 | 1 | 66 | 76 | |
| 1. ARC | R | | | 56 | 65 | |
| 2. SARANAC | S | | | 0 | 0 | |
| | TEST MEAN: | | | 41 | | |
| | L.S.D. (.05%) | | | 10 | | |
| | C.V. (%) (coefficient of variation) | | | 17 | | |

TEST CONDUCTED IN LAB GREENHOUSE.

*FIG. 2A*

BACTERIAL WILT
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1997 | 1 | 57 | 70 | 1.49 |
| 1. VERNAL | R | | | 34 | 42 | 2.20 |
| 2. SONORA | S | | | 1 | 1 | 4.16 |
| | TEST MEAN: | | | 31 | | 2.61 |
| | L.S.D. (.05%) | | | 10 | | 0.30 |
| | C.V. (%) | | | 12 | | 8.8 |

TEST CONDUCTED IN FIELD SPACE-PLANT NURSERY.

*FIG. 2B*

*FUSARIUM* WILT
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1997 | 1 | 60 | 64 | 1.97 |
| 1. AGATE | R | | | 51 | 54 | 2.19 |
| 2. MNGN-1 | S | | | 2 | 2 | 4.72 |
| | TEST MEAN: | | | 38 | | 2.96 |
| | L.S.D. (.05%) | | | 14 | | 0.43 |
| | C.V. (%) | | | 176 | | 13.7 |

TEST CONDUCTED IN FIELD SPACE-PLANT NURSERY.

*FIG. 2C*

VERTICILLIUM WILT
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | R | 1998 | 1 | 34 | 44 | 3.14 |
| 1. ONEIDA VR | R | | | 46 | 60 | 2.77 |
| 2. SARANAC | S | | | 3 | 4 | 3.98 |
| | TEST MEAN: | | | 28 | | 3.30 |
| | L.S.D. (.05%) | | | 11 | | 0.20 |
| | C.V. (%) | | | 22 | | 5.86 |

TEST CONDUCTED IN LAB GREENHOUSE.

*FIG. 2D*

PHYTOPHTHORA ROOT ROT
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1998 | 1 | 54 | 62 | |
| 1. WAPH-1 | R | | | 48 | 55 | |
| 2. SARANAC | S | | | 1 | 1 | |
| | TEST MEAN: | | | 34 | | |
| | L.S.D. (.05%) | | | 8 | | |
| | C.V. (%) | | | 12 | | |

TEST CONDUCTED IN LAB GREENHOUSE.

*FIG. 2E*

STEM NEMATODE
TEST CONDUCTED BY W-L RESEARCH AT WARDEN, WASHINGTON

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | R | 1998 | 1 | 41 | 40 | 3.1 |
| 1. VERNEMA | HR | | | 61 | 60 | 2.6 |
| 2. LAHONTAN | R | | | 37 | 36 | 3.3 |
| 3. RANGER | S | | | 7 | 7 | 4.2 |
| | TEST MEAN: | | | 37 | | 3.3 |
| | L.S.D. (.05%) | | | 13 | | 0.4 |

TEST CONDUCTED IN LAB GREENHOUSE.

*FIG. 2F*

APHANOMYCES ROOT ROT (RACE 1)
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1998 | 1 | 58 | 57 | 2.55 |
| 1. WAPH-1 | R | | | 51 | 50 | 3.07 |
| 2. AGATE | S | | | 0 | 0 | 4.86 |
| | TEST MEAN: | | | 36 | | 3.49 |
| | L.S.D. (.05%) | | | 10 | | 0.31 |
| | C.V. (%) | | | 19 | | 7.06 |

TEST CONDUCTED IN LAB GREENHOUSE.

*FIG. 2G*

APHANOMYCES ROOT ROT (RACE 2)
TEST CONDUCTED BY W-L RESEARCH AT EVANSVILLE, WISCONSIN

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | HR | 1998 | 1 | 53 | 66 | 3.42 |
| 1. WAPH-5 | R | | | 40 | 50 | 3.75 |
| 2. WAPH-1 | S | | | 0 | 0 | 4.70 |
| | TEST MEAN: | | | 31 | | 3.96 |
| | L.S.D. (.05%) | | | 9 | | 0.30 |
| | C.V. (%) | | | 15 | | 5.26 |

TEST CONDUCTED IN LAB GREENHOUSE.

*FIG. 2H*

PEA APHID
TEST CONDUCTED BY W-L RESEARCH AT BAKERSFIELD, CALIFORNIA

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | R | 1998 | 1 | 39 | 46 | 3.3 |
| 1. KANZA | R | | | 38 | 45 | 3.3 |
| 2. CALIVERDE | S | | | 0 | 0 | 4.9 |
| | TEST MEAN: | | | 26 | | 3.8 |
| | L.S.D. (.05%) | | | 7 | | 0.3 |
| | C.V. (%) | | | 10 | | 6.0 |

TEST CONDUCTED IN LAB GREENHOUSE.

*FIG. 2I*

SPOTTED ALFALFA APHID
TEST CONDUCTED BY W-L RESEARCH AT BAKERSFIELD, CALIFORNIA

| VARIETY | RESISTANCE CLASS | YEAR TESTED | SYN GEN | UNADJUSTED % R | ADJUSTED % R | SCORE OR A.S.I. |
|---|---|---|---|---|---|---|
| Test Variety WL-W316 | R | 1998 | 1 | 36 | 31 | 3.4 |
| 1. KANZA | R | | | 41 | 35 | 3.0 |
| 2. CALIVERDE | S | | | 0 | 0 | 4.9 |
| | TEST MEAN: | | | 26 | | 3.8 |
| | L.S.D. (.05%) | | | 2 | | 0.3 |
| | C.V. (%) | | | 3 | | 5.7 |

TEST CONDUCTED IN LAB GREENHOUSE.

*FIG. 2J*

STOCKTON, ILLINOIS
1998 WET CHEMISTRY DIGESTIBILITY RESULTS
SEEDED APRIL 1997

| ENTRY | % IN VITRO TRUE DIGESTIBILITY* |
|---|---|
| PIONEER 5347 LH | 75.6 |
| ABT 227 LH | 75.5 |
| WL-W316 | 75.4 |
| GH767 | 74.9 |
| AFFINITY + Z | 74.7 |
| PASSPORT | 74.4 |
| ABT 400 SCL | 74.2 |
| MAGNUM IV | 74.2 |
| PLATINUM | 73.9 |
| DK 140 | 73.7 |
| DK 141 (same as C105) | 72.9 |
| MEAN | 74.5 |
| L.S.D. (.10) | 2.0 |
| C.V. (%) | 2.3 |

\* IVTD (*IN VITRO* TRUE DIGESTIBILITY) IS A PROCEDURE THAT USES LIVING RUMEN MICROBES TO DIRECTLY MEASURE THE DIGESTIBILITY OF FORAGES. BECAUSE IT IS A DIRECT BIOLOGICAL MEASUREMENT OF THE TRULY DIGESTIBLE COMPONENTS OF A FORAGE, IVTD IS CONSIDERED THE MOST ACCURATE LABORATORY METHOD AVAILABLE FOR ESTIMATING THE FEEDING VALUE OF ALFALFA.

*FIG. 3A*

STOCKTON, ILLINOIS
1997 WET CHEMISTRY DIGESTIBILITY RESULTS
SEEDED APRIL 1997

| ENTRY | % IN VITRO TRUE DIGESTIBILITY* |
|---|---|
| WL-W316 | 71.5 |
| DK 141 (same as C105) | 70.3 |
| MEAN | 76.9 |
| L.S.D. (.10) | 1.2 |
| C.V. (%) | 4.3 |

*FIG. 3B*

ARLINGTON, WISCONSIN
1997 WET CHEMISTRY DIGESTIBILITY RESULTS
SEEDED APRIL 1997

| ENTRY | % IN VITRO TRUE DIGESTIBILITY* |
|---|---|
| WL-W316 | 78.0 |
| MAGNUM IV | 76.0 |
| PIONEER 5454 | 75.5 |
| AFFINITY + Z | 75.2 |
| MEAN | 76.2 |
| L.S.D. (.10) | 1.6 |
| C.V. (%) | 3.6 |

*FIG. 3C*

STOCKTON, ILLINOIS
1998 FORAGE QUALITY/MILK ECONOMICS RESULTS
SEEDED APRIL 1997

| ENTRY | CRUDE PROTEIN (%) | RELATIVE FEED VALUE | LBS. MILK PER ACRE | $ PER ACRE |
|---|---|---|---|---|
| WL-W316 | 17.5 | 148.9 | 12,155 | 1,823 |
| PLATINUM | 17.9 | 141.6 | 11,528 | 1,729 |
| AFFINITY + Z | 17.4 | 145.0 | 11,525 | 1,728 |
| PASSPORT | 17.2 | 137.9 | 11,345 | 1,702 |
| GH767 | 17.4 | 142.3 | 11,340 | 1,701 |
| ABT 227 LH | 18.0 | 146.4 | 11,320 | 1,698 |
| MAGNUM IV | 17.6 | 139.4 | 11,266 | 1,690 |
| ABT 400 SCL | 17.2 | 139.8 | 11,258 | 1,689 |
| DK 141 (same as C105) | 16.6 | 139.0 | 10,970 | 1,646 |
| MEAN | 17.4 | 142.3 | 11,412 | 1,712 |
| L.S.D. (.10) | 1.0 | 7.0 | | |
| C.V. (%) | 4.9 | 4.1 | | |

*FIG. 4*

MT. JOY, PENNSYLVANIA
1998 FORAGE YIELD RESULTS
SEEDED AUGUST 1997

| ENTRY | 1998 5-CUT TOTAL (T/A) |
|---|---|
| WL-W316 | 7.64 |
| AFFINITY + Z | 7.63 |
| STELLAR | 7.61 |
| ACCORD | 7.60 |
| PREFERRED | 7.60 |
| DK 141 | 7.57 |
| MEAN | 7.61 |
| L.S.D. (.05) | 0.41 |
| C.V. (%) | 3.80 |

*FIG. 5A*

EVANSVILLE, WISCONSIN VARIETY TRIAL
1997-98 FORAGE YIELD RESULTS, SEEDED APRIL 1997

| ENTRY | 1997-98 TOTAL YIELD (T/A) |
|---|---|
| WL-W316 | 8.74 |
| ABT 350 | 8.57 |
| WL 232 HQ | 8.39 |
| DK 141 | 8.31 |
| WL 326 GZ | 8.30 |
| PASSPORT | 8.28 |
| GH757 | 8.28 |
| WL 324 | 8.26 |
| BIGHORN | 8.26 |
| WL 325 HQ | 8.25 |
| RAINIER | 8.23 |
| MAGNUM IV | 8.18 |
| PIONEER 5454 | 8.18 |
| GH797 | 8.11 |
| AFFINITY + Z | 8.06 |
| ABT 400 SCL | 8.04 |
| AMERIGRAZE 401 + Z | 8.00 |
| WL 332 SR | 7.99 |
| GH767 | 7.95 |
| DK 140 | 7.88 |
| ABT 205 | 7.82 |
| DK 115 | 7.78 |
| ABT 227 LH | 7.77 |
| PIONEER 5347 LH | 7.76 |
| AMERIGUARD 301 | 7.54 |
| ARREST | 7.39 |
| MEAN | 8.09 |
| L.S.D. (.05) | 0.80 |
| C.V. (%) | 5.82 |

*FIG. 5B*

STOCKTON, ILLINOIS
1998 FORAGE YIELD RESULTS
SEEDED APRIL 1997

| ENTRY | 1998 4-CUT YIELD (T/A) |
|---|---|
| WL-W316 | 5.81 |
| MAGNUM IV | 5.81 |
| ABT 400 SCL | 5.80 |
| GH767 | 5.73 |
| ARREST | 5.71 |
| DK 141 | 5.69 |
| AFFINITY + Z | 5.68 |
| ABT 227 LH | 5.53 |
| MEAN | 5.72 |
| L.S.D. (.05) | 0.29 |
| C.V. (%) | 4.38 |

*FIG. 5C*

ARLINGTON, WISCONSIN
1997-98 FORAGE YIELD RESULTS
SEEDED APRIL 1997

| ENTRY | 1997-98 TOTAL YIELD (T/A) |
|---|---|
| WL-W316 | 8.65 |
| PLATINUM | 8.55 |
| PASSPORT | 8.48 |
| PIONEER 5454 | 8.46 |
| MAGNUM IV | 8.44 |
| WL 325 HQ | 8.37 |
| DK 127 | 8.35 |
| RAINIER | 8.35 |
| GH767 | 8.27 |
| WL 324 | 8.18 |
| ABT 227 LH | 8.17 |
| PIONEER 5347 LH | 8.00 |
| AFFINITY + Z | 7.95 |
| MEAN | 8.32 |
| L.S.D. (.05) | 0.55 |
| C.V. (%) | 6.85 |

*FIG. 5D*

ST. CHARLES, MINNESOTA
1997-98 FORAGE YIELD RESULTS
SEEDED APRIL 1997

| ENTRY | 1997-98 TOTAL YIELD (T/A) |
|---|---|
| WL-W316 | 8.57 |
| WL 232 HQ | 8.57 |
| RAINIER | 8.55 |
| GH757 | 8.47 |
| GH767 | 8.46 |
| STERLING | 8.45 |
| ABT 350 | 8.35 |
| WL 326 GZ | 8.32 |
| PIONEER 5347 LH | 8.31 |
| WL 324 | 8.27 |
| MAGNUM IV | 8.26 |
| LEGENDAIRY 2 | 8.16 |
| WL 325 HQ | 8.15 |
| DK 141 | 8.00 |
| ABT 227 LH | 7.96 |
| PASSPORT | 7.75 |
| MEAN | 8.29 |
| L.S.D. (.05) | 0.46 |
| C.V. (%) | 7.22 |

*FIG. 5E*

WARDEN, WASHINGTON
1998 FORAGE YIELD RESULTS
SEEDED AUGUST 1997

| ENTRY | 1998 4-CUT TOTAL (T/A) |
|---|---|
| RAINIER | 9.20 |
| WL-W316 | 9.11 |
| MULTI-PLIER II | 9.04 |
| LEAFMASTER | 9.01 |
| DK 141 | 8.61 |
| MEAN | 9.0 |
| L.S.D. (.05) | 0.97 |
| C.V. (%) | 7.33 |

*FIG. 5F*

ALFALFA LINE CALLED WL-W316 AND METHOD FOR PRODUCING SAME

FIELD OF THE INVENTION

This invention relates to the field of alfalfa plants, and more specifically to an improved synthetic alfalfa variety and a method for producing such a synthetic variety.

BACKGROUND OF THE INVENTION

Alfalfa (*Medicago sativa*) is an important and valuable forage and feed crop throughout the world. Alfalfa exhibits traits setting it apart from many other crop plants. It is an auto-tetraploid and is frequently self-incompatible in breeding. When selfed, little or no seed is produced, or the seed may not germinate, or when it does, it may later stop growing. Typically, fewer than five percent of selfed crosses produce seed. When a very small population is crossbred, inbreeding depression occurs, and traits of interest, such as quality, yield, and resistance to a large number of pests (e.g., seven or eight different pests), are lost. Thus, producing a true breeding parent for hybrids is not possible, which complicates breeding substantially.

Some sources indicate that there are nine major germplasm sources of alfalfa: *M. falcata,* Ladak, *M. varia,* Turkistan, Flemish, Chilean, Peruvian, Indian, and African. Tissue culture of explant source tissue, such as mature cotyledons and hypocotyls, demonstrates the regeneration frequency of genotypes in most cultivars is only about 10 percent. Seitz-Kris, M. H. and E. T. Bingham, *In vitro Cellular and Developmental Biology* 24 (10):1047–1052 (1988). Efforts have been underway to improve regeneration of alfalfa plants from callus tissue. E. T. Bingham, et. al., *Crop Science* 15:719–721 (1975).

Some methods for regeneration of alfalfa plants from tissue culture are described in U.S. Pat. No. 5,324,646 issued Jun. 28, 1994, which is hereby incorporated by reference. Certain other methods for generating alfalfa plants and seed are described in patent application Ser. No. 08/996,965 entitled "IMPROVED ALFALFA LINE CALLED WL-C290 AND METHOD FOR PRODUCING SAME" filed Dec. 23, 1997, and commonly assigned to the assignee of the present invention, which is hereby incorporated by reference.

Additionally, researchers believe that somatic embryogenesis in alfalfa is heritable, and is controlled by relatively few genes. Efforts at improving regeneration have thus been directed towards isolation of the genetic control of embryogenesis, and breeding programs which would incorporate such information. See, e.g., M. M. Hernandez-Fernandez, and B. R. Christie, *Genome* 32:318–321 (1989); I. M. Ray and E. T. Bingham, *Crop Science* 29:1545–1548 (1989).

Several genera of soilborne fungi can attack alfalfa seedlings, including Phytophthora, Pythium, Aphanomyces, Fusarium, and Rhizoctonia. Traditionally, Phytophthora and Pythium have been considered the most problematic pathogens, but recently *Aphanomyces euteiches* has been more widely recognized as a problem. According to one survey (referred to in Iowa State University's Integrated Crop Management Issue IC-478(5)—Apr. 21, 1997 (see http://www.ipm.iastate.edu/ipm/icm/1997/4-21-1997/alfalfa.html)), Aphanomyces is more common than Phytophthora in Iowa soils, and these two fungi should be considered equal threats to seedlings. Seedling diseases should be suspected when emergence is poor and/or there are obviously stunted, discolored, or dead seedlings. Like other crops, alfalfa seedling diseases are more severe in wet conditions. Unlike other crops, alfalfa seedlings are relatively cold-tolerant, therefore, it is not necessary to delay planting to avoid disease unless conditions are too wet. The best way to avoid seedling diseases is to plant varieties with a resistant (R) or highly resistant (HR) rating to both Phytophthora and Aphanomyces.

Alfalfa planted in poorly drained fields can succumb to root-rot fungi diseases such as Pythium, Phytophthora and Aphanomyces. Pythium (damping off) damage can be reduced with an Apron-brand (Metalaxyl) seed treatment. Phytophthora root rot can affect alfalfa at any age (seedling to adult plant). However, many established alfalfa varieties have high resistance to Phytophthora. Recently, Aphanomyces has been associated with seedling blight and poor seedling establishment. Even alfalfa stands with high levels of resistance to Phytophthora root rot can perform poorly in wet soils because of Aphanomyces. Unlike Phytophthora, Aphanomyces mainly affects the plant during the seedling stage. Aphanomyces root rot can be confused with mild herbicide damage, because the plants remain chlorotic and stunted. An alfalfa seedling infected with Aphanomyces root rot usually does not collapse and decay, as in damping off or Phytophthora root rot.

According to Dr. Craig Grau, Extension Plant Pathologist, the alfalfa Aphanomyces population includes two virulence types; Race 1 and Race 2. Race 1 forms are said to not cause severe disease on commercial varieties with an R or HR rating to Race 1 Aphanomyces root rot. Race 2 isolates cause severe disease on Race-1-resistant varieties in lab tests. Race-2-resistant breeding lines should out-yield Race-1-resistant varieties if Race 2 Aphanomyces is present or predominant in the soil.

High-quality alfalfa is alfalfa that is high in crude protein, high in digestibility, and low in acid and neutral-detergent fibre. Yield in alfalfa is measured as compared to check varieties, where greater than about 104%–105% of the check variety is considered high-yield.

Thus, there is a need for a high-yield, high-quality alfalfa that is resistant to Race 2 Aphanomyces root rot.

SUMMARY OF THE INVENTION

The present invention provides a semidormant, Dormancy-Group-3-type synthetic alfalfa variety, wherein one embodiment is named WL-W316, that provides greater feed value and improved yields under a variety of environmental conditions and, in particular, better resistance to the wet soil pathogen Race 2 Aphanomyces root rot. The primary uses of this WL-W316 variety are hay, haylage, greenchop and dehydrated feed for livestock.

The present invention also provides a method for breeding and selecting alfalfa in order to obtain resistance or high resistance to certain alfalfa pests. In particular, this method obtains a semidormant alfalfa variety that is high in forage quality and resistant to Race 2 Aphanomyces root rot.

In one embodiment, the present invention includes seed of synthetic alfalfa variety designated WL-W316 and having American Type Culture Collection (ATCC) 10801 University Boulevard, Manassas, Va. 20110-2209, received Jul. 15, 1998, Accession No. 203064. In another embodiment, the present invention includes an alfalfa plant or its parts produced by the seed of synthetic alfalfa variety designated WL-W316 or produced by regenerable plant parts of such seed. In yet other embodiments, the present invention includes pollen or an ovule of the plant produced by the seed of synthetic alfalfa variety designated WL-W316.

BRIEF DESCRIPTION OF THE DRAWINGS

FIG. 2A is a table comparing the test variety WL-W316 to other alfalfa varieties for resistance to Anthracnose (Race 1).

FIG. 2B is a table comparing the test variety WL-W316 to other alfalfa varieties for resistance to Bacterial Wilt.

FIG. 2C is a table comparing the test variety WL-W316 to other alfalfa varieties for resistance to Fusarium Wilt.

FIG. 2D is a table comparing the test variety WL-W316 to other alfalfa varieties for resistance to Verticillium Wilt.

FIG. 2E is a table comparing the test variety WL-W316 to other alfalfa varieties for resistance to Phytophthora Root Rot.

FIG. 2F is a table comparing the test variety WL-W316 to other alfalfa varieties for resistance to Stem Nematode.

FIG. 2G is a table comparing the test variety WL-W316 to other alfalfa varieties for resistance to Aphanomyces Root Rot (Race 1).

FIG. 2H is a table comparing the test variety WL-W316 to other alfalfa varieties for resistance to Aphanomyces Root Rot (Race 2).

FIG. 2I is a table comparing the test variety WL-W316 to other alfalfa varieties for resistance to Pea Aphid.

FIG. 2J is a table comparing the test variety WL-W316 to other alfalfa varieties for resistance to Spotted Alfalfa Aphid.

FIG. 3A is a table comparing the test variety WL-W316 to other alfalfa varieties for 1998 Wet Chemistry Digestibility Results for alfalfa seeded April 1997 at Stockton, Ill.

FIG. 3B is a table comparing the test variety WL-W316 to other alfalfa varieties for 1997 Wet Chemistry Digestibility Results for alfalfa seeded April 1997 at Stockton, Ill.

FIG. 3C is a table comparing the test variety WL-W316 to other alfalfa varieties for 1997 Wet Chemistry Digestibility Results for alfalfa seeded April 1997 at Arlington, Wis.

FIG. 4 is a table comparing the test variety WL-W316 to other alfalfa varieties for 1998 Forage Quality/Milk Economics Results for alfalfa seeded April 1997 at Stockton, Ill.

FIG. 5A is a table comparing the test variety WL-W316 to other alfalfa varieties for 1998 Forage Yield Results for alfalfa seeded August 1997 at Mt. Joy, Pa.

FIG. 5B is a table comparing the test variety WL-W316 to other alfalfa varieties for 1997–98 (total) Forage Yield Results for alfalfa seeded August 1997 at Evansville, Wis.

FIG. 5C is a table comparing the test variety WL-W316 to other alfalfa varieties for 1998 Forage Yield Results for alfalfa seeded April 1997 at Stockton, Ill.

FIG. 5D is a table comparing the test variety WL-W316 to other alfalfa varieties for 1997–98 (total) Forage Yield Results for alfalfa seeded April 1997 at Arlington, Wis.

FIG. 5E is a table comparing the test variety WL-W316 to other alfalfa varieties for 1997–98 (total) Forage Yield Results for alfalfa seeded April 1997 at St. Charles, Minn.

FIG. 5F is a table comparing the test variety WL-W316 to other alfalfa varieties for 1998 (4-cut total) Forage Yield Results for alfalfa seeded August 1997 at Warden, Wash.

DESCRIPTION OF THE PREFERRED EMBODIMENTS

Figure 1:
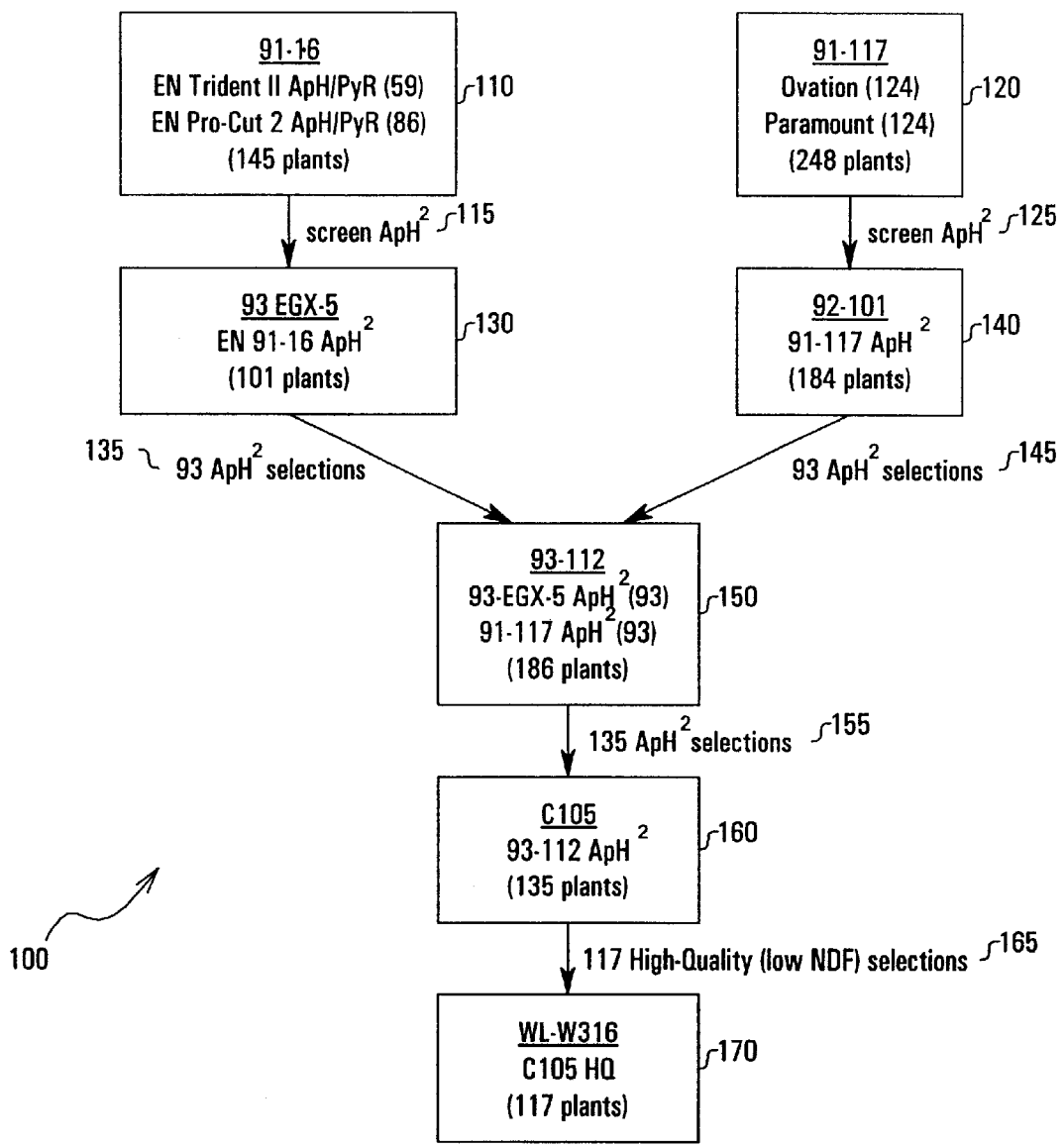
FIG. 1 shows a schematic representation of the breeding and selecting process for one embodiment of the present invention having a goal of producing a Dormancy Group 3 alfalfa with greater feed value and improved yields and better resistance to Race 2 Aphanomyces root rot.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The present invention provides a semidormant, Dormancy-Group-3-type synthetic alfalfa variety, wherein one embodiment is named WL-W316, that provides greater feed value and improved yields under a variety of environmental conditions and, in particular, better resistance to the wet soil pathogen Race 2 Aphanomyces root rot. The primary uses of this WL-W316 variety are hay, haylage, greenchop and dehydrated feed for livestock.

The present invention also provides a method for breeding and selecting alfalfa in order to obtain resistance or high resistance to certain alfalfa pests. In particular, this method obtains a semidormant alfalfa variety that is high in forage quality and resistant to Race 2 Aphanomyces root rot.

Alfalfa is classified into fall dormancy groups, numbered 1 to 10, where Dormancy Group 1 is very dormant and suited for cold climates (such varieties would stop growing and go dormant over winter), and Dormancy Group 10 is very non-dormant and suited for very hot climates (such varieties would have high growth rates over a very long growing season and would have relatively high winter activity). Until recently, the NAVRB (National Alfalfa Variety Review Board), which recently changed its name to "National Alfalfa and Miscellaneous Legume Variety Review Board" (NA&MLVRB), recognized standard or check varieties for Dormancy Groups 1–9, but did not have a standard check variety for Group 10. Check cultivars are listed in the NAAIC *Standard Tests to Characterize Alfalfa Cultivars*, 3rd Edition, as amended, July 1998. (NAAIC is the North America Alfalfa Improvement Conference, which is the governing body over the NAVRB, (National Alfalfa Variety Review Board, which recently changed its name to "National Alfalfa and Miscellaneous Legume Variety Review Board" (NA&MLVRB)). The check varieties for the various fall dormancy ratings/ Dormancy Groups (corresponding to the rating scale used by the Certified Alfalfa Seed Council (CASC)) are as follows:

Check Cultivars

A single set of check cultivars representing fall dormancy classes (FDC) 1 to 11 are designated. These check cultivars have been selected to maintain the intended relationship between the original set of nine check cultivars (Standard Tests, March 1991) and to have minimal variation across environments. The actual fall dormancy rating (FDR) based on the average University of California regression and the Certified Alfalfa Seed Council Class that each check cultivar represents are listed below.

| Variety | FDR[1] | FDC[2] |
|---|---|---|
| Maverick | 0.8 | 1.0 |
| Vernal | 2.0 | 2.0 |
| 5246 | 3.4 | 3.0 |
| Legend | 3.8 | 4.0 |
| Archer | 5.3 | 5.0 |
| ABI 700 | 6.3 | 6.0 |
| Dona Ana | 6.7 | 7.0 |
| Pierce | 7.8 | 8.0 |
| CUF101 | 8.9 | 9.0 |
| UC-1887 | 9.9 | 10.0 |
| UC-1465 | 11.2 | 11.0 |

[1]Number corresponds to the value calculated using the University of California regression equation.
[2]Number corresponds to fall dormancy class used by the Certified Alfalfa Seed Council (CASC).

WL-W316 Alfalfa—Technical Description

WLW316 is synthetic variety alfalfa derived from 117 high-yielding and persistent plants selected for high forage quality (high % crude protein, low acid and low Neutral-Detergent Fiber, or "NDF"). The WL-W316 synthetic variety alfalfa is the result of recurrent phenotypic selection for resistance to Aphanomyces root rot (Race 2) carried out in a greenhouse screening at Evansville, Wis., U.S.A. Subsequent selection (second cycle) was performed for resistance to Aphanomyces root rot (Race 2) in a greenhouse screening at Evansville, Wis. Then, 117 plants were selected for high yield (i.e., to increase the yield or tons of alfalfa per acre that could be harvested), high percentage crude protein content, low acid content, and low NDF. The 117 plants used as parental selections were grown in an isolation cage at Bakersfield, Calif. and breeder seed was produced using bee pollination. Breeder seed (synthetic generation 1, or "Syn 1") was bulked (all seed from all plants are mixed) following harvest in year 5 (year numbers herein are referenced to an arbitrarily chosen "year 1" of the breeding program).

One generation of Breeder seed (Syn 1) and two generations each of Foundation seed (Syn 2 or 3) and Certified seed (Syn 3 or 4) are recognized by the inventors. The maximum permitted length of stand for Foundation and Certified seed fields are 3 and 5 years, respectively. Foundation (Syn 2) seed was produced at Warden Washington in sufficient quantity for the life of the WL-W316 variety and will be maintained by W-L Research, Inc. The ATCC Designation of the seed is "WL-W316."

The primary uses of plants of the WL-W316 variety are hay, haylage, greenchop and dehydration.

Genetic source material for WL-W316 traces to two high-yielding, winter-hardy lines that were selected for resistance to Aphanomyces root rot (Race 2). Parental germplasm traces to Trident II, Pro-Cut 2, Ovation and Paramount, with breeding and selection steps as shown in FIG. 1.

FIG. 1 shows pedigree flowchart for WL-W316 having a breeding method 100. At block 110, fifty-nine (59) plants of Trident II are crossed with eighty-six (86) plants of Pro-Cut 2. At block 120, one hundred twenty-four (124) plants of Ovation are crossed with one hundred twenty-four (124) plants of Paramount.

Trident II is a commercially released available product of ABI, Inc., Napier, Iowa. The approximate geimplasm source contributions for Trident II are: M. falcata—10%; Ladak—10%; M. varia—21%; Turkistan—17%; Flemish—35%; Chilean—4%; and Peruvian—3%. Pro-Cut 2 is a commercially released and available product of Research Seeds, Inc., St. Joseph, Mo. Approximate germplasm source contributions are: M. falcata—4%; Ladak—3%; M. varia—25%; Turkistan—3%; Flemish—59%; and Chilean—6%. Paramount is a commercially released and available product of W-L Research, Inc., Evansville, Wis. Approximate germplasm source contributions are: M. falcata—4%; Ladak—16%; M. varia—23%; Turkistan—4%; Flemish—48%; and Chilean—5%. Ovation is a commercially released and available product of W-L Research, Inc., Evansville, Wis. Approximate germplasm source contributions are: M. falcata—10%; Ladak—17%; M. varia—23%; Turkistan—8%; Flemish—37%; and Chilean—5%.

At step 115, a large number of seeds resulting from cross 110 are planted, and the resulting plants are selected for resistance to Race 2 Aphanomyces root rot. One-hundred-one (101) of the most Race-2-Aphanomyces-root-rot resistant plants from step 115 are crossed with one another in step 130. Similarly, at step 125, a large number of seeds resulting from cross 120 are planted, and the resulting plants are selected for resistance to Race 2 Aphanomyces root rot. One-hundred-eighty-four (184) of the most Race-2-Aphanomyces-root-rot resistant plants from step 125 are crossed with one another in step 140.

At step 135, a large number of seeds resulting from cross 130 are planted, and the resulting plants are selected for resistance to Race 2 Aphanomyces root rot. Ninety-three (93) of the most Race-2-Aphanomyces-root-rot resistant plants from step 135 are input to step 150. Similarly, at step 145, a large number of seeds resulting from cross 120 are planted, and the resulting plants are selected for resistance to Race 2 Aphanomyces root rot. Ninety-three (93) of the most Race-2-Aphanomyces-root-rot resistant plants from step 145 are input to step 150, and crossed with the ninety-three (93) plants from step 135.

At step 155, a large number of seeds resulting from cross 150 are planted, and the resulting plants are selected for resistance to Race 2 Aphanomyces root rot. One-hundred-thirty-five (135) of the most Race-2-Aphanomyces-root-rot resistant plants from step 155 are crossed with one another in step 160. At step 165, a large number of seeds resulting from cross 160 are planted, and the resulting plants are selected for low Neutral-Detergent Fiber (NDF). One-hundred-seventeen (117) of the lowest NDF plants from step 165 are crossed with one another in step 170, and Breeder seed (synthetic generation 1, or "Syn 1") was bulked from all seed from all one-hundred-seventeen (117) plants.

Approximate germplasm source contributions to WL-W316 are thought to be: M. falcata—8%; Ladak—17%; M. varia—29%; Turkistan—5%; Flemish—38%; and Chilean—5%.

The flower color at full bloom of WL-W316 at synthetic generation two (Syn 2) approaches 100% purple with traces of white and variegated. (See USDA Agriculture Handbook No. 424—A System for Visually Classifying Alfalfa Flower Color.) At full bloom, WL-W316 is approximately 100% purple, trace white, 0% yellow, trace variegated, 0% cream.

The fall dormancy class that WYL-W316 is most similar to is Fall Dormancy Class 3 (FD3).

WL-W316 has high resistance to bacterial wilt, Fusarium wilt, anthracnose, Phytophthora root rot, Aphanomyces root rot (Race 1) and Aphanomyces root rot (Race 2); and resistance to verticillium wilt, pea aphid, spotted alfalfa aphid and stem nematode.

Under field conditions, WL-W316 displays resistance (no stunting or yellowing, significantly improved seedling vigor and stand establishment) to both Race 1 and Race 2 Aphanomyces root rots.

WL-W316 is a winter hardy, persistent and high-yielding variety. WL-W316 is also the first highuality alfalfa release selected to display resistance to Race 2 Aphanomyces root rot.

Pedigree and Method Used to Create WL-W316

FIG. 1 shows a schematic representation of the breeding and selecting process for one embodiment of the present invention having a goal of producing a high-quality, Dormancy Group 3 alfalfa that is resistant to Race 2 Aphanomyces root rot.

FIGS. 2A–2J, 3A–3D, 4, and 5A–5F (described mode fully below) show additional information pertaining to alfalfa WL-W316. Specifically, FIGS. 2A–2J compare resistances to various pests and diseases, and FIGS. 3A–3D, 4, and 5A–5F compare WL-W316 and DK 141 for forage yield and forage quality performance in trials across the Midwest and in Washington state.

WL-W316 is 100% derived from DK 141 (also called C105), as shown on the breeding flowchart of FIG. 1. DK 141 was screened for greater digestibility and high yield potential, with selected plants used to produce WL-W316. Experimental WL-W316 demonstrates higher forage yield and greater digestibility when compared to DK 141. Resistance to Aphanomyces Root Rot Race 2 is similar between the two lines but is still a major differentiating factor from other alfalfas on the market.

Measurements of Alfalfa Nutritive Value

Crude Protein ("C?") is determined by measuring the total nitrogen concentration of a forage and multiplying it by 6.25. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to a ruminant animals from a given forage.

Acid-Detergent Fiber ("ADF") approximates the amount of fiber present in a feed that is indigestible. Forages with high ADF values are less digestible than forages with low ADF values and, therefore, provide fewer nutrients to the animal through digestion. Because of this relationship, ADF serves as an estimate of digestibility and can be used by nutritionists to predict the energy that will be available from a forage.

Neutral-Detergent Fiber ("NDF") represents the total amount of fiber present in the alfalfa. Because fiber is the portion of the plant most slowly digested in the rumen, it is this fraction that fills the rumen and becomes a limit to the amount of feed an animal can consume. The higher the NDF concentration of a forage, the quicker the rumen will fill and the less an animal will be able to consume. For this reason, NDF is used by nutritionists as an estimate of the quantity of forage that an animal will be able to consume. Forages with high NDF levels can limit intake to the point that an animal is unable to consume enough feed to meet their energy and protein requirements.

Relative Feed Value ("RFV") is a numeric value assigned to forages based upon their ADF and NDF values. In this calculation, NDF is used to estimate the dry matter intake expected for a given forage and the ADF concentration is used to estimate the digestibility of the forage. By combining these two relationships, an estimate of digestible dry matter intake is generated. This value is then reported relative to a standard forage (fall bloom alfalfa=100) and can be used to rank forages based on their anticipated feeding value. Relative feed value has been accepted in many areas as a means of estimating forage feeding value and is commonly used in determining the price of alfalfa at tested hay auctions.

In Vitro True Digestibility (IVTD) is a measurement of digestibility utilizing actual rumen microorganisms. Although ADF serves as a good estimate of digestibility, IVID provides a more accurate assessment of a forage's feeding value by actually measuring tie portion of a forage that is digested. This process is more expensive and time consuming than the analysis for ADF concentrations of a feed, but provides a more meaningful measure of forage digestibility. Techniques for measuring in vitro digestibility are based on incubating a forage sample in a solution containing rumen microorganisms for an extended period of time (usually 48 hours).

Total Digestible Nutrients (TDN) is an estimate of the energy content of a feedstuff based on its relative proportions of fiber, fat, carbohydrate, crude protein, and ash. Because it is expensive to measure each of these components, TDN is usually estimated from ADF or IVTD. Although still used in some areas as a criteria for evaluating alfalfa hay at auctions, TDN has been shown to overestimate the energy content of low quality forages and thus does not accurately reflect the nutritional value of all forage samples.

Milk Per Ton is an estimate of the milk production that could be supported by a given forage when fed as part of a total mixed ration. The equation for calculating milk per ton uses NDF and ADF to calculate total energy intake possible from the forage. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. Milk per ton is useful because it characterizes forage quality in two terms that a dairy farmer is familiar with: pounds of milk and tons of forage. By combining milk per ton and dry matter yield per acre, we arrive at "milk per acre". This term is widely used to estimate the economic value of a forage.

FIG. 1 shows a schematic representation of the breeding and selecting process for one embodiment of the present invention having a goal of producing a Dormancy Group 3 alfalfa with greater feed value and improved yields and better resistance to Race 2 Aphanomyces root rot.

FIG. 2A is a table comparing the test variety WL-W316 to other alfalfa varieties for resistance to Anthracnose (Race 1).

FIG. 2B is a table comparing the test variety WL-W316 to other alfalfa varieties for resistance to Bacterial Wilt.

FIG. 2C is a table comparing the test variety WL-W316 to other alfalfa varieties for resistance to Fusanum Wilt.

FIG. 2D is a table comparing the test variety WL-W316 to other alfalfa varieties for resistance to Verticillium Wilt.

FIG. 2E is a table comparing the test variety WL-W316 to other alfalfa varieties for resistance to Phytophthora Root Rot.

FIG. 2F is a table comparing the test variety WL-W316 to other alfalfa varieties for resistance to Stem Nematode.

FIG. 2G is a table comparing the test variety WL-W316 to other alfalfa varieties for resistance to Aphanomyces Root Rot (Race 1).

FIG. 2H is a table comparing the test variety WL-W316 to other alfalfa varieties for resistance to Aphanomyces Root Rot (Race 2).

FIG. 2I is a table comparing the test variety WL-W316 to other alfalfa varieties for resistance to Pea Aphid.

FIG. 2J is a table comparing the test variety WL-W316 to other alfalfa varieties for resistance to Spotted Alfalfa Aphid.

FIG. 3A is a table comparing the test variety WL-W316 to other alfalfa varieties for 1998 Wet Chemistry Digestibility Results for alfalfa seeded April 1997 at Stockton, Ill. The IVTD (In Vitro True Digestibility) measurement shown in these tables is a test procedure that uses living rumen microbes to directly measure the digestibility of forages. Because it is a direct biological measurement of the truly digestible components of a forage, IVTD is considered the most accurate laboratory method available for estimating the feeding value of alfalfa.

FIG. 3B is a table comparing the test variety WL-W316 to other alfalfa varieties for 1997 Wet Chemistry Digestibility Results for alfalfa seeded April 1997 at Stockton, Ill.

FIG. 3C is a table comparing the test variety WL-W316 to other alfalfa varieties for 1997 Wet Chemistry Digestibility Results for alfalfa seeded April 1997 at Arlington, Wis.

FIG. 4 is a table comparing the test variety WL-W316 to other alfalfa varieties for 1998 Forage Quality/Milk Economics Results for alfalfa seeded April 1997 at Stockton, Ill.

FIG. 5A is a table comparing the test variety WL-W316 to other alfalfa varieties for 1998 Forage Yield Results for alfalfa seeded August 1997 at Mt. Joy, Pa.

FIG. 5B is a table comparing the test variety WL-W316 to other alfalfa varieties for 1997–98 (total) Forage Yield Results for alfalfa seeded August 1997 at Evansville, Wis.

FIG. 5C is a table comparing the test variety WL-W316 to other alfalfa varieties for 1998 Forage Yield Results for alfalfa seeded April 1997 at Stockton, Ill.

FIG. 5D is a table comparing the test variety WL-W316 to other alfalfa varieties for 1997–98 (total) Forage Yield Results for alfalfa seeded April 1997 at Arlington, Wis.

FIG. 5E is a table comparing the test variety WL-W316 to other alfalfa varieties for 1997–98 (total) Forage Yield Results for alfalfa seeded April 1997 at St. Charles, Minn.

FIG. 5F is a table comparing the test variety WL-W316 to other alfalfa varieties for 1998 (4-cut total) Forage Yield Results for alfalfa seeded August 1997 at Warden, Wash.

As used herein, the variety designated DK141 is the same as the variety designated C105 (see, e.g., FIG. 1 step 160, and the table in FIG. 3A).

Conclusion

In one embodiment, the present invention is seed of synthetic alfalfa variety designated WL-W316 and having American Type Culture Collection (ATCC) Accession No. 203064.

In another embodiment, the present invention is an alfalfa plant produced by the seed of synthetic alfalfa variety designated WL-W316 and having American Type Culture Collection (ATCC) Accession No. 203064 or regenerable parts of said seed. Other separate embodiments include seed of such an alfalfa plant, pollen of such an alfalfa plant and seed of an alfalfa plant pollinated by such pollen, and an ovule of such an alfalfa plant. Yet other embodiments include an alfalfa plant having all the physiological and morphological characteristics of such an alfalfa plant and such an alfalfa plant that is male sterile.

Yet another embodiment is a tissue culture of regenerable cells, where the cells include genetic material conveying resistance to Aphanomyces (Race 2) derived, in whole or in part, from an alfalfa plant of synthetic variety named WL-W316 (the seed of which have been deposited and have ATCC Accession No. 203064). In one such embodiment, the cells regenerate plants having substantially all the morphological and physiological characteristics of the synthetic alfalfa variety named WL-W316 that are described in the attached FIGS. 2A–2J, 3A–3C, 4, and 5A–5F. Some embodiments include such a tissue culture that includes cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts. Another embodiment is an alfalfa plant regenerated from such a tissue culture, having all the morphological and physiological characteristics of synthetic alfalfa variety WL-W316.

Another aspect of the present invention provides a method for producing first-generation synthetic variety alfalfa seed comprising crossing a first parent alfalfa plant with a second parent alfalfa plant and harvesting resultant first-generation (F1) hybrid alfalfa seed, wherein said first or second parent alfalfa plant is one of the alfalfa plants of the present invention described above.

Still another aspect of the present invention provides an alfalfa plant having resistance to Aphanomyces Race 2), forage yield, and In Vitro True Digestibility substantially equal to or better than corresponding respective characteristics of one of the alfalfa plants of the present invention described above.

Yet another aspect of the present invention provides a method for breeding and selecting alfalfa comprising the steps of:

(a) crossing plants of Trident II variety with plants of Pro-Cut 2 variety to obtain germplasm;
(b) growing one or more generations of alfalfa plants from the germplasm resulting from the cross of step (a);
(c) selecting alfalfa plants from step (b) for resistance to Race 2 Aphanomyces root rot;
(d) crossing plants of Ovation variety with plants of Paramount variety to obtain germplasm;
(e) growing one or more generations of alfalfa plants from the germplasm resulting from the cross of step (d);
(f) selecting alfalfa plants from step (e) for resistance to Race 2 Aphanomyces root rot;
(g) crossing plants resulting from step (c) with plants resulting from step (f) to obtain germplasm;
(h) growing one or more generations of alfalfa plants from the germplasm resulting from the cross of step (g);
(i) selecting, from among the plants resulting from step (h), a first population of plants that are lower in Neutral-Detergent Fiber (NDF) and thus higher in feed value than other plants resulting from step (h); and
(j) crossing the first population of plants of step (i) amongst themselves to obtain seed.

In some such embodiments, the steps (a) through (j) just described are performed in the order indicated. In other embodiments, the order is different. In some embodiments, the method also includes (h1) one or more further cycles selecting for resistance to Race 2 Aphanomyces root rot, and in some embodiments, the step (h1) is performed between steps (h) and (i).

Another aspect of the present invention provides an alfalfa plant or its parts produced by the seed produced by one of the forms of the just-described method or regenerable parts of said seed. Other separate embodiments include seed of such an alfalfa plant, pollen of such an alfalfa plant and seed of an alfalfa plant pollinated by such pollen, and an ovule of such an alfalfa plant. Yet other embodiments include an alfalfa plant having all the physiological and morphological characteristics of such an alfalfa plant and such an alfalfa plant that is male sterile.

Yet another aspect of the present invention provides an alfalfa plant or its parts produced by the seed produced by one of the embodiments of the just-described method, wherein this plant exhibits resistance to Aphanomyces (Race 2), forage yield, and In Vitro True Digestibility substantially equal to or better than corresponding respective characteristics of alfalfa variety designated WL-W316, the seed of which have been deposited and have ATCC Accession No. 203064.

Yet another aspect of the present invention provides seed of one or more alfalfa plants, wherein the seed comprises genetic material conveying resistance to Aphanomyces (Race 2) derived at least in part from alfalfa variety designated WL-W316, the seed of which have been deposited and have ATCC Accession No. 203064. In some such embodiments, the seed is produced by a cage-cross breeding program. Another such embodiment is an alfalfa plant, or parts thereof, produced by such seed or regenerable parts of said seed.

Still another aspect of the present invention provides a method for breeding and selecting alfalfa. This method includes (a) growing one or more generations of alfalfa plants having genetic material derived from Trident II alfalfa variety, Pro-Cut 2 alfalfa variety, Ovation alfalfa variety, and Paramount alfalfa variety, to obtain germplasm;

(b) selecting alfalfa plants from step (a) for resistance to Race 2 Aphanomyces root rot;

(c) crossing plants resulting from step (b) with one another to obtain germplasm;

(d) growing one or more generations of alfalfa plants from the germplasm resulting from the cross of step (c);

(e) selecting, from among the plants resulting from step (d), a first population of plants that are lower in Neutral-Detergent Fiber (NDF) and higher in feed value than other plants resulting from step (d); and (f) crossing the first population of plants of step (f) amongst themselves to obtain seed.

Other embodiments include an alfalfa plant or its parts produced from the seed of this method or regenerable parts of said seed. Still another embodiment is seed of such an alfalfa plant, or of successive generations, that derive resistance to Race 2 Aphanomyces root rot from such an alfalfa plant. Yet another embodiment is pollen of such a plant that conveys resistance to Race 2 Aphanomyces root rot. One embodiment is seed of an alfalfa plant pollinated by such pollen.

Yet another embodiment is an alfalfa plant to which resistance to Race 2 Aphanomyces root rot has been transferred from a parent plant or succeeding generations thereof grown from a seed of alfalfa variety designated WL-W316, the seed of which have been deposited and have ATCC Accession No. 203064.

Still another embodiment is an alfalfa plant having an adjusted resistance to Race 2 Aphanomyces root rot of about 59% or greater, an in vitro true digestibility (IVTD) about one L.S.D. (0.10) or more above that of variety WL-C105, and a crude protein content of about 17% or greater. Other such embodiments include an alfalfa plant further having an unadjusted resistance to Race 2 Aphanomyces root rot of about one L.S.D. (0.05%) or more better than that of WAPH-5 alfalfa variety (see FIG. 2H). Other such embodiments include an alfalfa plant further having an IVTD of about 75% or greater. Other such embodiments include an alfalfa plant further having an IVTD of about 74% or greater. Other such embodiments include an alfalfa plant further having an IVTD of about 73% or greater. Other such embodiments include an alfalfa plant further having a crude protein content of about 17.25% or greater. Still other such embodiments include an alfalfa plant further having a crude protein content of about 17.5% or greater.

The references listed below are incorporated herein by reference to the extent that they supplement, explain, provide a background for, or teach methodology, techniques, and/or compositions employed herein:

Armstrong and Green, (1985). "Establishment and Maintenance of Friable, Embryogenic Maize Callus and the Involvement of L-Proline," Planta, 164:207–214.

Chu, C. C., Wang, C. C., Sun, C. S., et al. (1975). Scientia Sinica 18:659–668.

Coe, E. H., et al (1988) "The Genetics of Corn and Corn Improvement", 3rd. ed., Vol. 18, Sprague and Dudley (eds.) 87:258

Duvick, D. N. (1984) "Genetic Contribution to Yield Gains of U.S. Hybrid Maize-1930–1980," Genetic Contribution to Yield Gains of Five Major Crops, pp. 15–48.

Finkle, B. J., Ulrich, J. M., Rains, W., et al. (1985). Plant Sci. 42:133–140.

Goodman, M. and Stuber, C., "Genetic Identification of Lines and Crosses Using Isoenzyme Electrophoresis," Proceedings of the Thirty-Fifth Annual Corn and Sorghum Industry Research Conferences, Chicago, 1980.

Gordon-Kamm, W. et al., (1990) "Transformation of Maize Cells and Regeneration of Fertile Transgenic Plants," The Plant Cell, V.2, 603–618.

Hauptmann, R. M., Vasil, V., Ozias-Aikins, P., et al. (1988). Plant Physiol. 86:602–606.

Klein, T. M., Kornstein, L., Sanford, J. C., et al. (1989). Plant Physiol. 91:440444.

Murashige, T. and Skoog, F. (1962). Plant Physiol. 15:473–497.

Rhodes, C. A., Pierce, D. A., Mettler, F. J., et al. (1988). Science 240:204–207.

Roberts, Nuc. Acids Res. 10:117–144 (1982).

Troyer, A. F. (1990) "A Retrospective View of Corn Genetic Resources" Journal of Heredity, 81: 17–24

Withers, L. A., King, P. J. (1979). Plant Physiol. 64:675–678.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. Bleed of synthetic alfalfa variety designated WL-W316 and having American Type Culture Collection (ATCC) Accession No. 203064.

2. An alfalfa plant produced by the seed of claim 1 or regenerable parts of said seed.

3. Seed of the alfalfa plant of claim 2.

4. Pollen of the plant of claim 2.

5. Seed of an alfalfa plant pollinated by the pollen of claim 4.

6. An ovule of the plant of claim 2.

7. An alfalfa plant having all the physiological and morphological characteristics of the plant of claim 2.

8. The alfalfa plant of claim 2 that is male sterile.

9. A tissue culture of regenerable cells, the cells comprising genetic material <conveying resistance to Aphanomyces (Race 2) derived, in whole or in part, from an alfalfa plant of synthetic variety named WL-W316, the seed of which have been deposited and have ATCC Accession No. 203064.

10. A tissue culture of claim 9, comprising cultured cells derived, in whole or in part, from a plant part selected from the group consisting of leaves, roots, root tips, root hairs, anthers, pistils, stamens, pollen, ovules, flowers, seeds, embryos, stems, buds, cotyledons, hypocotyls, cells and protoplasts.

11. An alfalfa plant regenerated from the tissue culture of claim 9, having all the morphological and physiological characteristics of synthetic alfalfa variety WL-W316.

12. A method for producing first-generation synthetic variety alfalfa seed comprising crossing a first parent alfalfa plant with a second parent alfalfa plant and harvesting resultant first-generation (F1) hybrid alfalfa seed, wherein said first or second parent alfalfa plant is the alfalfa plant of claim 2.

13. Seed of one or more alfalfa plants, wherein the seed comprises genetic material conveying resistance to Aphanomyces (Race 2) derived at least in part from alfalfa variety designated WL-W316, the seed of which have been deposited and have ATCC Accession No. 203064.

14. The seed of claim 13, wherein the seed is produced by a cage-cross breeding program.

15. An alfalfa plant produced by the seed of claim 13 or regenerable parts of said seed.

16. Parts of an alfalfa plant produced by the seed of claim 13 or regenerable parts of said seed.

17. Seed of the alfalfa plant of claim 15.

18. An alfalfa plant to which resistance to Race 2 Aphanomyces root rot has been transferred from a parent plant or succeeding generations thereof grown from a seed of alfalfa variety designated WL-W316, the seed of which have been deposited and have ATCC Accession No. 203064.

19. Seed of the alfalfa plant of claim 18.

20. An alfalfa plant grown from the seed of claim 19 or regenerable parts of said seed and having resistance to Aphanomyces (Race 2), forage yield, and In Vitro True Digestibility substantially equal to corresponding respective characteristics of alfalfa variety designated WLW316, the seed of which have been deposited and have ATCC Accession No. 203064.

21. Parts of an alfalfa plant produced by the seed of claim 19 regenerable parts of said seed.

22. Pollen of the plant of claim 18.

23. Seed of an alfalfa plant pollinated by the pollen of claim 22.

24. An alfalfa plant grown from the seed of claim 17 or regenerable parts of said seed and having resistance to Aphanomyces (Race 2), forage yield, and In Vitro True Digestibility substantially equal to corresponding respective characteristics of alfalfa variety designated WLW316, the seed of which have been deposited and have ATCC Accession No. 203064.

25. Pollen of the plant of claim 24.

26. Seed of an alfalfa plant pollinated by the pollen of claim 25.

27. Parts of an alfalfa plant produced by the seed of claim 17 or regenerable parts of said seed.

28. Seed of the alfalfa plant of claim 11.

29. An alfalfa plant grown from the seed of claim 28 or regenerable parts of said seed and having resistance to Aphanomyces (Race 2), forage yield, and In Vitro True Digestibility substantially equal to corresponding respective characteristics of alfalfa variety designated WL-W316, the seed of which have been deposited and have ATCC Accession No. 203064.

30. Parts of an alfalfa plant produced by the seed of claim 28 or regenerable parts of said seed.

31. Seed of the alfalfa plant of claim 7.

32. Parts of an alfalfa plant produced by the seed of claim 31 or regenerable parts of said seed.

33. An alfalfa plant grown from the seed of claim 3 or regenerable parts of said seed and having resistance to Aphanomyces (Race 2), forage yield, and In Vitro True Digestibility substantially equal to corresponding respective characteristics of alfalfa variety designated WL-W316, the seed of which have been deposited and have ATCC Accession No. 203064.

34. Parts of an alfalfa plant produced by the seed of claim 3 or regenerable parts of said seed.

35. Parts of an alfalfa plant produced by the seed of claim 1 or regenerable parts of said seed.

* * * * *